United States Patent [19]

Fortier et al.

[11] Patent Number: 4,661,110

[45] Date of Patent: Apr. 28, 1987

[54] MULTIPLE PASSAGE CONNECTOR FITTING FOR A MEDICAL TUBE

[75] Inventors: Earl J. Fortier, Tucson, Ariz.; Robert D. Banning, St. Peters, Mo.

[73] Assignee: Sherwood Medical Company, St. Louis, Mo.

[21] Appl. No.: 733,564

[22] Filed: May 13, 1985

[51] Int. Cl.⁴ ............................................. A61M 25/00
[52] U.S. Cl. .................................. 604/256; 604/284; 604/905
[58] Field of Search ............... 604/403, 905, 280, 326, 604/283, 256, 284; 222/484

[56] References Cited

U.S. PATENT DOCUMENTS

| | | | |
|---|---|---|---|
| 3,058,472 | 10/1962 | Thornton, Jr. | 604/283 |
| 3,625,793 | 12/1971 | Sheridan | 156/229 |
| 4,349,024 | 9/1982 | Ralston, Jr. | 604/905 |
| 4,407,281 | 10/1983 | Brandt et al. | 128/207.15 |
| 4,560,378 | 12/1985 | Weiland | 604/256 |

OTHER PUBLICATIONS

USCI, Extracorporeal Circulation Cannulae and Vinyl Specialty Catheters (Section 7) pamphlet.

Primary Examiner—Stephen C. Pellegrino
Assistant Examiner—John D. Ferros
Attorney, Agent, or Firm—Stanley N. Garber; Andrew J. Beck; William R. O'Meara

[57] ABSTRACT

A multiple passage tube connector fitting is provided which includes a pair of connectors each having a passage open at one end. The fitting has a single-piece elastomeric tube adapter and plug device having a coupling element for connecting it to the connector. The device includes a tube adapter having a passage through it which is connected by a flexible strap to the coupling element and is adapted to fit in the passage of the connector. Another plug is connected by a strap to theadapter for closing the adapter passage. The device also has a plug connected to the coupling element by flexible strap for closing the passage of the other connector.

18 Claims, 6 Drawing Figures

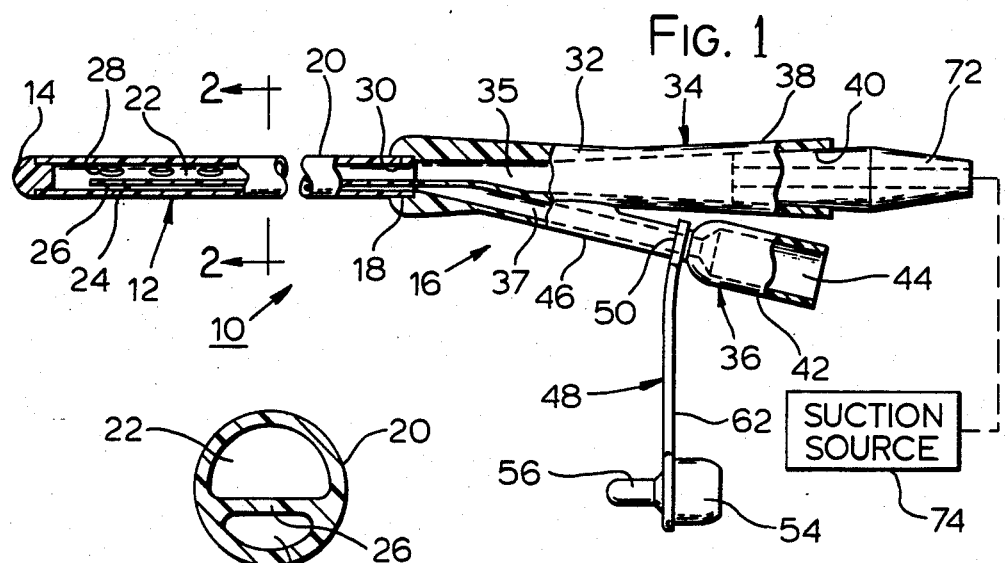
FIG. 1
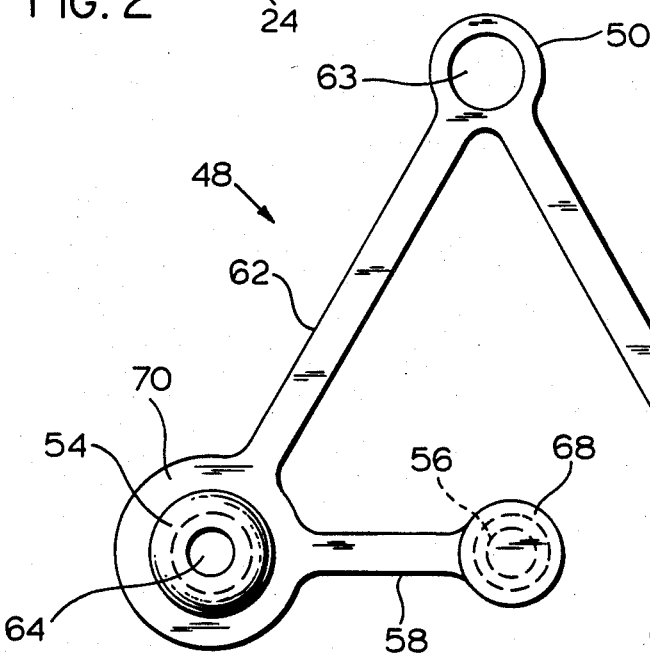
FIG. 2
FIG. 3
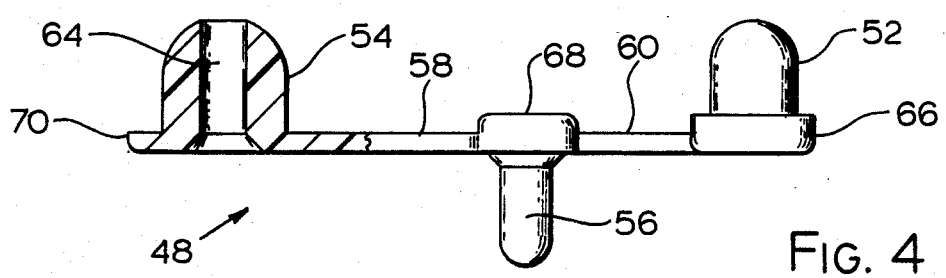
FIG. 4

MULTIPLE PASSAGE CONNECTOR FITTING FOR A MEDICAL TUBE

DESCRIPTION

1. Technical Field

This invention relates to multiple passage connector fittings for multiple tubes and more particularly to such connector fittings having tube adapter and cap devices associated with them.

2. Background Art

As is well known, dual lumen sump tubes or catheters can be used for a number of purposes, for examle, aspirating fluids from the stomach, feeding the patient, decompression and irrigation. Sump tubes have primary and secondary lumens whereby, for aspiration purposes for example, a source of suction may be connected to the primary lumen while the secondary lumen is vented to the atmosphere. If desired, the secondary lumen may be used to introduce irrigation fluids into the stomach while the primary lumen is connected to a suction source. When feeding the patient, the liquid food may be introduced through the primary lumen while the secondary lumen is closed. In order to use the sump tube for these and other functions, various connections to the lumens at the proximal end of the sump tube are required. In the past, the closing and opening of the various lumens and connecting the primary lumen with relatively large and small size connectors has been cumbersome. A variety of parts including plugs and adapters have been used but they have been relatively complicated and expensive, and in some cases, plugs and connectors could be misplaced or lost.

SUMMARY OF THE INVENTION

It is therefore an object of the present invention to provide an improved multiple lumen connector fitting for a medical tube having closure caps as well as a tube adapter connected to the fitting and which substantially overcomes the above-mentioned problems or disadvantages.

Another object of the present invention is to provide an improved sump tube having an improved tube adapter and cap device for facilitating the use of the tube for various purposes.

In accordance with one aspect of the present invention, a connector fitting for a tube is provided with a pair of connectors having passages therein, and a tube adapter and cap device connected to the fitting. The tube adapter and cap device includes a tube adapter having a passage and that can be inserted into one of the connector passages, and a plug for insertion into the adapter passage to close it when desired. The tube adapter and cap device also has a plug which can be used to close the other connector passage when desired.

These, as well as other objects and advantages of the present invention, will become apparent from the following detailed description and accompanying drawings.

BRIEF DESCRIPTION OF THE DRAWINGS

FIG. 1 is a side elevation of a medical sump tube connected to a connector fitting in accordance with a preferred embodiment of the present invention;

FIG. 2 is a cross-sectional view, on an enlarged scale, taken along the line 2—2 of FIG. 1;

FIG. 3 is a top plan view, on an enlarged scale, of the tube adapter and plug device of the fitting of FIG. 1;

FIG. 4 is a bottom plan view, partly in section, of the device of FIG. 3;

DESCRIPTION OF THE PREFERRED EMBODIMENT

Figure 5:
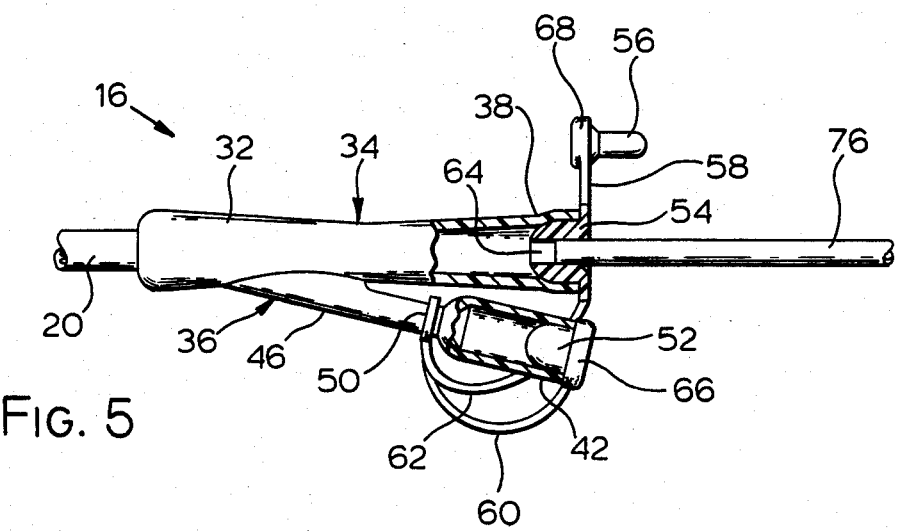
FIG. 5 is a fragmentary plan view of the proximal portion of the connector fitting of FIG. 1 with a portion thereof in cross-section and showing the tube adapter and one plug of the device inserted into the fitting of FIG. 1.

Referring now to the drawings, and particularly FIGS. 1 and 2, there is shown a sump tube 10 including a tube or catheter 12 having a smoothly rounded tip 14 at the distal end and a multiple passage connector or fitting 16 connected to the proximal end, indicated at 18, of tube 12.

The tube 12 includes a flexible tubular shaft or tube 20 having a primary lumen 22 and a smaller secondary lumen 24, the lumens being separated by an integral wall 26 which extends from the proximal end 18 to a point near the distal end of the shaft and such that the secondary lumen 24 is in fluid communication with the primary lumen 22 only adjacent the distal end of the tube 12. The shaft 20 has a plurality of openings 28 which extend through its sidewall and connect with primary lumen 22. The distal end or tip 14 may be a preformed member which may be of the same material as that of shaft 20 and be secured in place by an adhesive, solvent bonding or by other means. The proximal end 18 of shaft 20 may be secured by adhesive, solvent bonding or by other means within a socket 30 in the distal end of the connector fitting 16. Tube shaft 20 may be made from a number of suitable materials and is preferably formed from a suitable elastomeric material, such as natural or synthetic rubber, and preferably from silicone rubber. Other plastic materials such as thermoplastic material, for example, a polyvinyl chloride may also be used.

The multiple lumen connector fitting 16 is shown including a single-piece, generally 'Y' connector body 32 having a main connector 34 with a main passage 35 and a secondary connector 36 with a secondary passage 37, the main and secondary passages being connected in fluid communication with tube lumens 22 and 24, respectively. The main passage 35 is shown larger in size than the lumen 37. The main a connector 34 has a distal end connector portion or socket 38 having a tapered bore 40 which connects with passage 35. Connector 36 has an enlarged end connector portion or socket 42 having a bore 44 which connects with passage 37. Connector 36 is shown extending angularly from the axis of connector 34 and in spaced relation from connector 34. Connector 36 includes a connecting tube portion 46 smaller than and integrally connecting the socket 42 to the distal end portion of body 32. The connector 34 is larger or has a greater outer diameter than that of the connecting portion 46.

Connector fitting 16 also includes a tube adapter and plug device indicated generally at 48 and which is best shown in FIGS. 3 and 4 where the device 48 is shown alone. As seen in FIG. 3, the device 48 is a single-piece member substantially triangular in shape in its molded form or at rest but with one leg open. The device has a coupling element shown as a ring 50 at the upper corner, a closure or plug 52 at a bottom corner, a tube adapter 54 at the other bottom corner of the triangle, and a plug 56 integrally connected by a flexible strap 58 to the adapter 54. The strap 58 extends longitudinally along a line that substantially intersects the plug 52 and adapter 54. Plug 52 is connected by a flexible strap 60 to the coupling member 50 and the adapter 54 is connected by a flexible strap 62 to the coupling element 50. The tube adapter 54 has a passage 64 extending through it which is adapted to receive, when the adapter is in use, a tube connector (not shown) or the plug 56. The coupling ring 50 has an opening 63 sized to fit over and surround the connecting tube portion 46 of connector 36. By making the device 48 of elastomeric material, the coupling ring 50 can be stretched or expanded to fit over the socket 42 and onto the connecting tube portion 46 as shown in FIG. 1. The coupling ring 50 has an opening 63 which is smaller than the outer diameter of socket 42 so that when located on the narrower tube portion 46, the ring cannot inadvertently come off of the fittin or be misplaced or lost.

Plug 52 is shaped for insertion into the bore 44 of socket 42 of connector 36 to plug or close the proximal end of passage 37. Tube adapter 54 is adapted to sealingly fit into the bore 40 of socket 38 of connector 34 so that a connector of relatively small size or outer diameter can be inserted into tight fitting relation in the passage 64 of the adapter in fluid communication with passage 35. Plug 56 is sized and adapted to fit in the distal end of a passage 64 in the tube adapter 54. The plugs 52 and 56 and adapter 54 are provided with enlarged integral annular flanges 66, 68 and 70, respectively, which may be conveniently grasped by the fingers when inserting or removing them from passages. The tube adapter and plug device 48 may be made of a suitable rubber or plastic and is preferably made of an elastomeric material such as silicone rubber.

In FIG. 1, the device 48 is shown in its inactive condition, that is, it is tethered by coupling element 50 to the connection tube 46 but the plugs 52 and 56 and the tube adapter 54 are not in their respective passages of the device.

A tube coupler 72 is shown with one end inserted into socket 40 of the main connector portion 38 and schematically connected to a suction source 74. The coupler 72 has conical or tapered ends so that the distal end forms a fluid-tight connection with bore 40 while the tapered proximal end is adapted to connect with tubing of various sizes that may be used in suction systems.

In use, when the tube 12 is inserted into the stomach and the suction source connected to the main connector 38, as in FIG. 1, fluids in the stomach will flow into the openings 28 at the distal end of the catheter 12 and flow through the main lumen 22 and passage 35 to the suction source which may include a collection system including a container for receiving the aspirated fluid. During aspiration, the secondary connector 42 may be open to the atmosphere as shown so that the secondary lumen 24 is vented to the atmosphere. This tends to prevent invagination of tissue, tends to reduce the negative pressure within the stomach to avoid excessive negative pressures and, in general, aids the aspiration function.

When it is desired to connect the sump tube 10 to a feeding bag or pump set, the tube coupler 72 may be removed from bore 40 of main connector portion 38 and the tube adapter 54 of device 48 inserted in tight-fluid connection in bore 40. This, in effect, provides the connector portion or socket 38 with a smaller passage or bore, that is, with passage 64 of the adapter and allows the relatively small tubing generally associated with feeding bags or pump sets to be inserted into the passage 64 in fluid tight connection. As illustrated in FIG. 5, a tube 76 of reduced size is shown connected in sealing engagement with the walls of opening 64 to connect a feeding bag or pump set with the main passage 35 and primary lumen 22. In FIG. 5 the plug 52 is shown for illustration closing the secondary connector 42 to close off the secondary lumen 24 of tube 12 from the atmosphere. Closing the secondary lumen may be done during feeding.

Figure 6:
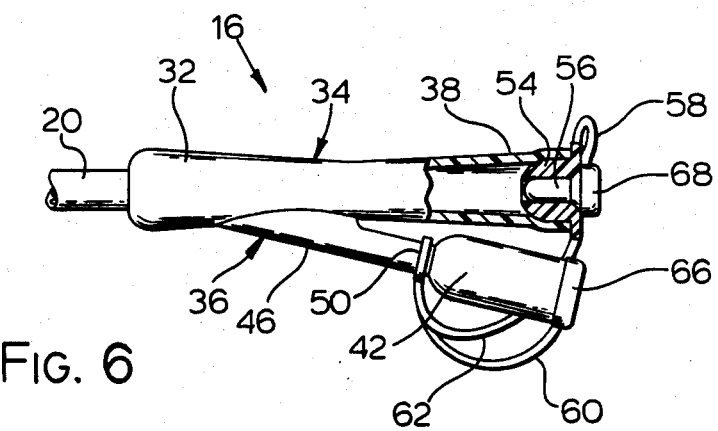
FIG. 6 is a plan view similar to that of FIG. 5 but with a second plug closing the adapter.

In FIG. 6, the tube adapter 54 is shown disposed in the main connector portion 38, the plug 56 is shown inserted into the passage 64 in the adapter 54, and the plug 52 is shown closing the secondary connector 42. In this way both connectors 34 and 36, and therefore both tube lumens 22 and 24, are closed off from atmosphere. The connectors 34 and 36 may be closed in this manner when it is desired to transport the patient or during the time between successive feedings. The sump tube 10 illustrated may, of course, be used for various other purposes and in different manners from those mentioned above.

The sump tube 10 with the tube adapter and plug device 48 is versatile in use as mentioned previously herein and the plugs and adapter cannot be misplaced but rather are always associated with the sump tube for use. Both plugs 52 and 56 and tube adapter 54 are integrally connected together in a compact manner. By molding the device 48 in a substantially triangular configuration in its molded shape or at rest, (FIG. 3) the size of the mold used to make it can be of a more economical size.

As various changes could be made in the above described construction without departing from the true spirit and scope of the invention, it is intended that all matter contained in the above description and shown in the accompanying drawings be interpreted as illustrative.

What is claimed is:

1. A multiple passage fitting for a medical tube comprising a body including a first connector having a first passage therethrough and a connector portion at the proximal end thereof for connection to another member, a second connector having a second passage therethrough and a connector portion at the proximal end thereof for connection with another member, and a tube adapter and closure cap device including a first flexible strap connected to said fitting, a tube adapter connected to said first strap and adapted to fit in said connector portion of said first connector in fluid tight connection therewith, said tube adapter having a third passage therethrough connected with said first passage and adapted for connection with another member when said tube adapter is in said connector portion of said first connector, a second flexible strap connected to said tube adapter, a first closure plug connected to said second strap and adapted to fit in said third passage to close the same, a third flexible strap connected to said fitting, a second closure plug connected to said third strap and adapted to fit in said connector portion of said second connector to close said second passage, and both of said first and third straps connected to said second connector by coupling means connected to said first and third straps for connecting said tube adapter and cap device to said second connector.

2. The fitting od claim 1 wherein said first passage is of larger diameter than that of said second passage.

3. The fitting of claim 2 wherein said second connector is connected to said first connector adjacent the distal end thereof and extends in spaced relation to said first connector.

4. The fitting of claim 3 wherein said coupling means comprises an elastomeric ring surrounding a part of said second connector.

5. The connector of claim 4 wherein said second connector includes a socket connected to a connecting portion of smaller diameter than said second socket and which connects said socket with said fitting, and said ring is distally of said socket and of smaller diameter than that of said socket, said ring surrounding said connecting portion.

6. The connector of claim 5 wherein said second connector extends at an angle to said first connector.

7. A multiple passage fitting for a medical tube comprising a body including a first connector having a first passage therethrough and a connector portion at the proximal end thereof for connection to another member, a second connector having a second passage therethrough and a connector portion at the proximal end thereof for connection with another member, and a tube adapter and closure cap device including a first flexible strap connected to said fitting, a tube adapter connected to said first strap and adapted to fit in said connector portion of said first connector in fluid tight connection therewith, said tube adapter having a third passage therethrough connected with said first passage and adapted for connection with another member when said tube adapter is in said connector portion of said first connector, a second flexible strap connected to said tube adapter, a first closure plug connected to said second strap and adapted to fit in said third passage to close the same, a third flexible strap connected to said fitting, a second closure plug connected to said third strap and adapted to fit in said connector portion of said second connector to close said second passage, said tube adapter and closure cap device being a single-piece device and further including an elastic ring connected to said first and third straps and surrounding a part of said fitting.

8. The connector of claim 7 wherein said tube adapter and closure device is of an elastomeric material and is removably insertable onto said fitting.

9. The connector of claim 7 wherein said device is of silicone rubber.

10. The connector of claim 7 wherein said first, second and third straps are capable of assuming a generally substantially triangular configuration but with said first plug spaced from said second plug.

11. A sump tube comprising a tube shaft having a primary lumen and a secondary lumen of smaller cross-section than that of said primary lumen communicating therewith adjacent the distal end thereof, said shaft having openings in the side wall thereof near the distal end thereof connecting with said primary lumen, and a fitting connected to the proximal end of said shaft and having first and second connectors said connectors having first and second passages connected to said primary and secondary lumens, respectively, said first and second connectors having first and second connector portions open at the proximal ends, and a separate single-piece elastomeric tube adapter and cap device including a tube adapter removably insertable into said first connector portion in sealing engagement therewith and having an opening therethrough connectable with said first passage, a first plug removably insertable into said opening for closing the same, a first strap connecting said first plug to said tube adapter, a second plug removably insertable into said second connector portion for closing the same, a coupling element for connection to a said fitting, and second and third straps respectively connecting said tube adapter and said second plug to said coupling element.

12. The tube of claim 11 wherein said coupling element is connectable to second connector.

13. The tube of claim 11 wherein said second connector includes a connecting portion connecting said second connector portion to said fiting and having a smaller outer diameter than said second connector portion, and said coupling element includes a ring surrounding said connecting portion distally of said second connector portion to secure said tube adapter and closure cap device to said fitting.

14. The tube of claim 11 wherein said coupling element is an elastic ring surrounding a port od said second conductor.

15. The tube of claim 11 wherein said shaft and said fitting are of silicone rubber.

16. A single-piece tube adapter and cap device of elastomeric material for a multiple passage connector fitting having a pair of passages for connection at the distal ends with another member and open at the proximal ends thereof comprising a coupling element for connection to the fitting, a first flexible strap integrally connected to said element, a tube adapter integrally connected to said first strap and including a plug adapted to be inserted into the open end of one of the passages of the fitting and having a passage therethrough, a second flexible strap integrally connected to said tube adapter, a first plug connected to said second strap in spaced relation with said tube adapter and adapted to be inserted into said tube adapter passage to close the same, a third strap integrally connected to said coupling element, and a second plug integrally connected to said third strap and adapted to be inserted into the open end of the other of the passage of the fitting to close the same.

17. The device of claim 16 wherein said coupling element is a ring stretchable over a part of the fitting for securing said device.

18. The device of claim 17 wherein said straps are angularly related to each other in a substantially triangular configuration.

* * * * *